US012247941B2

(12) United States Patent
Mucic et al.

(10) Patent No.: US 12,247,941 B2
(45) Date of Patent: Mar. 11, 2025

(54) GLUCOSE BIOSENSOR ENCASEMENT, GLUCOSE BIOSENSOR PACKAGE, AND METHOD

(71) Applicant: Medtronic MiniMed, Inc., Northridge, CA (US)

(72) Inventors: Robert Mucic, Glendale, CA (US); Zhenzhong Sun, Northridge, CA (US); Akhil Srinivasan, Woodland Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 208 days.

(21) Appl. No.: 16/691,403

(22) Filed: Nov. 21, 2019

(65) Prior Publication Data

US 2021/0156815 A1    May 27, 2021

(51) Int. Cl.
*A61B 5/145* (2006.01)
*G01N 27/31* (2006.01)
*G01N 27/327* (2006.01)

(52) U.S. Cl.
CPC ..... *G01N 27/3273* (2013.01); *A61B 5/14532* (2013.01); *G01N 27/31* (2013.01); *A61B 2560/0406* (2013.01); *A61B 2562/16* (2013.01); *A61B 2562/18* (2013.01)

(58) Field of Classification Search
CPC ..... A61B 5/145; A61B 5/1451; A61B 5/1468; A61B 5/1473; A61B 5/14735; A61B 5/1477; A61B 5/1486; A61B 5/14532; A61B 2560/0406; A61B 2562/16; A61B 2562/18; A61B 5/14865; G01N 27/3273; G01N 27/31

See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |

(Continued)

OTHER PUBLICATIONS

C. Gonzalez, S.D. Collins, R.L. Smith, "Fluidic interconnects for modular assembly of chemical microsystems", 1998, (Year: 1998).*

*Primary Examiner* — David J. McCrosky
(74) *Attorney, Agent, or Firm* — GATES & COOPER LLP

(57) ABSTRACT

A glucose biosensor encasement includes a first membrane and a second membrane. The first membrane has a first interlocking segment. The second membrane has a second interlocking segment cooperating with the first interlocking segment of the first membrane to provide a cavity between the first membrane and the second membrane configured to receive a glucose sensor. At least one of the first membrane and the second membrane comprises a semi-permeable portion configured to regulate diffusion characteristics of glucose through the membrane to realize a sensitivity for a sensor in the cavity. A method is also provided.

14 Claims, 2 Drawing Sheets

(56) References Cited

U.S. PATENT DOCUMENTS

| | | |
|---|---|---|
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,757,056 B1* | 9/2017 | Kubba ................. A61B 5/6821 |
| 2004/0054352 A1* | 3/2004 | Adams ................. A61B 5/0028 |
| | | 604/891.1 |
| 2007/0123819 A1 | 5/2007 | Mernoe et al. |
| 2010/0160861 A1 | 6/2010 | Causey, III et al. |
| 2014/0128760 A1* | 5/2014 | Saunders ............... A61B 5/082 |
| | | 600/532 |
| 2014/0135606 A1* | 5/2014 | Yasui ................. A61B 5/14532 |
| | | 600/365 |
| 2015/0276651 A1* | 10/2015 | Petisce ............... G01N 27/3272 |
| | | 216/13 |
| 2015/0328632 A1* | 11/2015 | Kurata ............. G01N 33/48764 |
| | | 435/309.1 |
| 2017/0356839 A1* | 12/2017 | Hennings ........... G01N 21/7703 |
| 2018/0000395 A1* | 1/2018 | Lucisano ........... A61B 5/14542 |
| 2018/0099278 A1* | 4/2018 | Niemeyer ........... B01J 19/0093 |
| 2019/0117131 A1* | 4/2019 | Halac .................... G01N 33/66 |

\* cited by examiner

GLUCOSE BIOSENSOR ENCASEMENT, GLUCOSE BIOSENSOR PACKAGE, AND METHOD

CROSS REFERENCE TO RELATED APPLICATION

This application does not claim priority from any other application.

TECHNICAL FIELD

The subject matter of this application pertains to detection and concentration of analytes in mammals. More particularly, the subject matter relates to the detection and concentration measurement of glucose within a mammal.

BACKGROUND OF THE DISCLOSURE

Mammals are known to have cellular sensors that self-detect chemical constituents of the body, in particular tissues or blood, so that the body can control changes in constituent concentrations. However, disease and pathophysiological states can impart deviations from normal concentrations of constituents in bodily tissues and blood. Techniques are known for detecting blood glucose levels associated with diabetes. Further similar bodily malfunctions are also desired to be detected so that therapy and diagnostics can be implemented for patients. However, further improvements are needed to increase accuracy and longevity of inserted sensors when measuring constituents and physical membrane lamination and permeability issues can negatively affect performance.

SUMMARY

A sensor encasement and package is provided for measuring analytes, such as glucose, in the body of mammals that improves reliability and useable life over previously known techniques. Interlocking segments are provided near sensing elements and/or along membrane edges to prevent peeling up of edge layers that could otherwise negatively influence side diffusion of components, or analytes, like glucose that would reduce sensor accuracy and calibration.

In one aspect, glucose biosensor encasement includes a first membrane and a second membrane. The first membrane has a first interlocking segment. The second membrane has a second interlocking segment cooperating with the first interlocking segment of the first membrane to provide a cavity between the first membrane and the second membrane configured to receive a glucose sensor. At least one of the first membrane and the second membrane comprises a semi-permeable portion configured to regulate diffusion characteristics of glucose through the membrane to realize a sensitivity for a sensor in the cavity.

In another aspect, a glucose biosensor package is provided having a first membrane and a second membrane. The first membrane has a first interlocking portion. The second membrane has a second interlocking portion cooperating with the first interlocking portion of the first membrane to provide a cavity between the first membrane and the second membrane configured to receive a biosensor. The biosensor has at least one sensing element contained in the cavity. At least one of the first membrane and the second membrane comprises a semi-permeable portion configured to regulate diffusion characteristics of glucose through the membrane to realize a sensitivity for a sensor in the cavity.

In yet another aspect, a method is provided for encasing a biosensor. The method includes: providing a first membrane with an interlocking segment proximate a sensing element having an undercut width; depositing a second membrane into the interlocking segment and over the first membrane and the sensing element; and interlocking the second membrane with the first membrane along the interlocking segment to mitigate edge lifting of the first membrane relative to the second membrane.

These and other aspects are contemplated and described herein. It will be appreciated that the foregoing summary sets out representative aspects of a system and method for detecting releasable coupling of a cap with an insulin delivery device and assists skilled readers in understanding the following detailed description.

DETAILED DESCRIPTION OF THE EMBODIMENTS

This disclosure is submitted in furtherance of the constitutional purposes of the U.S. Patent Laws "to promote the progress of science and useful arts" (Article 1, Section 8).

As used herein, the terms "portion" and "segment" refer to any structure capable of providing an interlocking interface along a discrete span or an encircling span that joins unto itself, such as a circle, oval, square, rectangle or other suitable geometric shape capable of substantially adjoining or encompassing a sensor region, and can also include discrete enlarged head posts and complementary entrapping ports.

Figure 1:
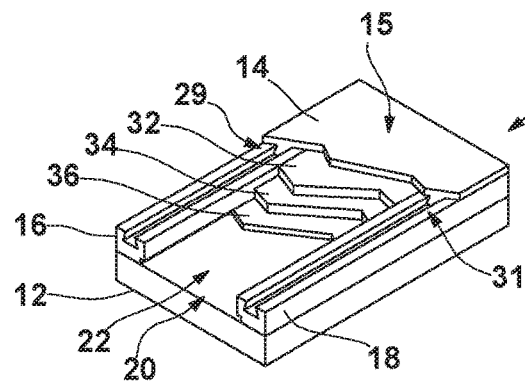
FIG. 1 is a perspective view from above of a glucose sensor encasement with a substrate membrane layer having an interlocking trench pattern in a base insulation layer for encasing an in-vivo sensor to mitigate membrane layer peeling proximate electrodes of a glucose limiting membrane interlock with the base insulation layer.

FIG. 1 illustrates a glucose sensor encasement having a substrate layer, or membrane 12 interlocked with a glucose limiting membrane (GLM) 14 according to one aspect. Membrane 14 comprises a semi-permeable portion 15 configured to regulate diffusion characteristics of glucose through membrane portion 15 to realize a sensitivity for a sensor in a cavity, or trench 20. Layer 12 supports a pair of spaced-apart and interlocking segments, or elongate dovetail rails 16 and 18. Elongate cavity, or trench 20 is provided between rails 16 and 18 configured to receive a sensor 22 comprising one or more sensing elements, or electrodes as depicted in FIGS. 7-11, such as GOx sensor 22 of FIG. 7 and is formed from deposited mask layers comprising a glucose oxidase enzyme layer 32, a platinum layer 34, and a gold layer 36. Accordingly, a mechanical locking feature is provided between layers 12 and 14 that prevents peeling apart of such layers proximate a sensing electrode of sensor 22.

As used herein, any form of membrane can be dovetail joined to another surface or membrane in order to substantially encase or secure or adhere edges or local portions of such membranes from pulling apart during use, and does not necessarily need to be limited to use on sensor limiting membranes. It is also understood that raised portions can be substituted for depressions, or grooves (and vice versa) when implementing such dovetail mechanical locking feature between two or more membranes.

Figure 4:
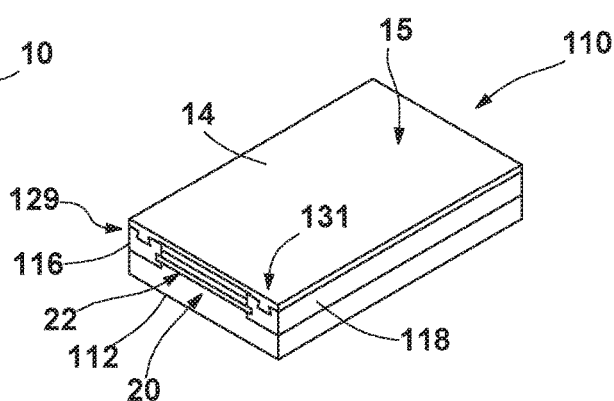
FIG. 4 is a perspective view from above of another glucose sensor encasement having a slightly modified substrate membrane over that shown in FIGS. 1-3 with an interlocking trench pattern in a base insulation layer, a glucose limiting membrane interlocked with the base insulation layer, and a sensing electrode encased between the interlocked membrane layers.
Figure 2:
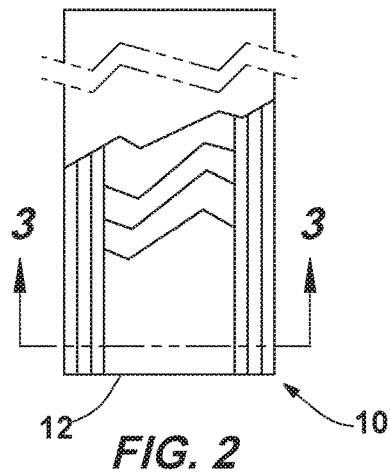
FIG. 2 is a plan view of the substrate membrane layer of FIG. 1 with the top layer and sensor removed.
Figure 5:
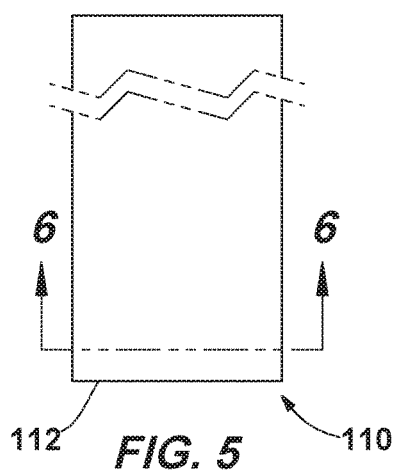
FIG. 5 is a plan view of the substrate membrane layer of FIG. 4.
Figure 3:
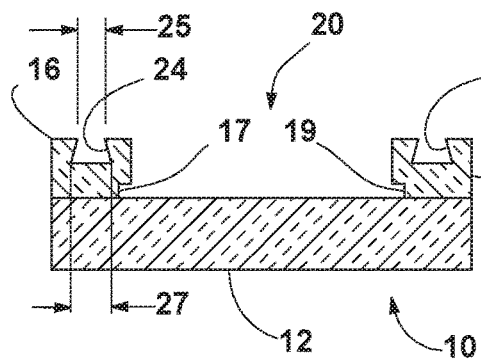
FIG. 3 is a vertical sectional view taken along line 3-3 of FIG. 2.
Figure 6:
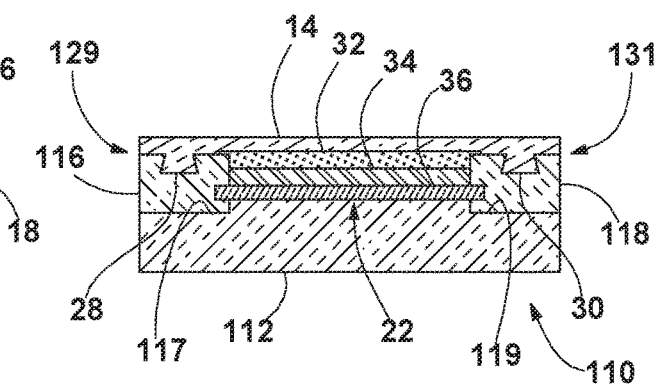
FIG. 6 is a vertical sectional view taken along line 6-6 of FIG. 5.

FIG. 3 illustrates a vertical sectional view taken along line 3-3 of FIG. 2 one suitable geometry of substrate layer 12 of encasement 10 with layer 14 and sensor 22 removed. As shown in FIG. 3, dovetail interlocking segments, or rails 16 and 18 are affixed to an insulation polymer layer, or substrate layer 12. Optionally, such segments 16 and 18 can be integrally formed on top of layer 12. Either way, an elongate undercut structural feature, or undercut mechanical interlock, is formed in segments 16 and 18 represented as a dovetail having an ensmalled width 25 distal of layer 12 and an enlarged width 27 proximal layer 12. A sensor 22 (see FIG. 4) is then deposited in layers atop layer 12 and between segments 16 and 18 (as shown in FIGS. 4-6) after which a top layer, or membrane 14 is deposited atop and within rails 16 and 18 to interlock and encase sensor 22 between layers 12 and 14. According to one construction layer 12 and segments 16 and 18 are constructed from polyimide, an insulation layer patterned to receive one of the mask layout sensor designs depicted in FIGS. 7-11, such as sensor 22 in FIG. 7.

As shown in FIG. 3, layer 12 can be deposited in a first mask layer after which segments 16 and 18 are deposited on top of layer 12 in a second mask layer that also includes an undercut mechanical interlock 17 and 19 configured to entrap layer 36 onto layer 12. An epoxy or acrylic flexible adhesive can be added to layer, for example, layer 12 can be a polyimide layer configured as a coverlay having an adhesive layer. Segments 16 and 18 can also be made of polyimide. Optionally, to reduce alignment variation and simplify the process, segments 16 and 18 can be added to the insulation pattern mask layer for membrane 12 so that segments 16 and 18 are aligned in recessed channels 17 and 19 and layer 12 and rails 16 and 18 form a monolithic layer.

As shown in FIG. 4, glucose biosensor encasement 110 is shown assembled together with a glucose limiting membrane (GLM) 14 interlocked with insulation layer 12 on opposed edges along sensor 22 using opposed interlocking elongate segment assemblies 29 and 31. Membrane 14 comprises a semi-permeable membrane layer that forms a chamber for at least one sensing element to hold a reactant that reacts with an analyte to measure concentration of a reaction product with the sensing element, or sensor 22. The semi-permeable membrane allows passage of the analyte into the chamber where byproducts of a reaction can be detected and quantified. Each assembly 29 and 31 includes an interlocking dovetail 16 and 18 and an entrapped elongate tenon, or ridge 28 and 30 (see FIG. 6) that provides a physical, or mechanical interlock between layers in order to prevent any leakage along the edges and adjacent sensing elements that would otherwise make such byproduct detection inaccurate, such as when detecting glucose levels.

As detailed in FIG. 5, FIG. 6 shows the interlocked assembly in vertical sectional view through encasement 10 and internal sensor 22. Sensor is provided in an assembled mask deposition layer configuration comprising a glucose oxidase enzyme layer 32, a platinum layer 34, and a gold layer 36. Deposition of layer 14 into dovetail segments 16 and 18 locks edges of layers 12 and 14 together adjacent to sensor 22 which prevents peeling of layers 12 and 14 in use in vivo within a patient. Such peeling otherwise reduces accuracy of sensor 22.

Although a classic dovetail geometry is provided within interlocking segments 16 and 18, it is understood that any cross-sectional geometry that has an ensmalled distal portion and an enlarged proximal portion (relative to layer 12) will provide such an interlocking physical geometry suitable to prevent peeling of layers 12 and 14, such as a cylindrical or elliptical elongate groove shape sized to entrap a complementary male elongate rope, or tenon portion, and can include octagonal, hexagonal, triangular, or any other interlocking geometry grooves and complementary tenons.

As shown in FIG. 6, glucose biosensor encasement 10 includes a first membrane 112 and a second membrane 14. First membrane 112 has a first interlocking segment 116 and 118. Second membrane 14 has a second interlocking segment 28 and 30 cooperating with the first interlocking segment 116 and 118 of the first membrane 112 to provide a cavity 20 (see FIGS. 1 and 4) between first membrane 112 and second membrane 14 for receiving a glucose sensor 22. Interlocking segment pairs 129 and 131 are provided when segments 28 and 30 are deposited within segments 116 and 118 respectively during a semiconductor/mask deposition operation. At least one of first membrane 112 and second membrane 14 comprises a semi-permeable portion 15 (see FIG. 4) configured to regulate diffusion characteristics of glucose through membrane 14 to realize a sensitivity for sensor 22 in cavity 20. A pair of elongate recess slots 117 and 119 are formed in membrane, or layer 112 to receive each interlocking segment 116 and 118 in alignment when deposited atop layer 112 during a deposition step from a mask operation.

Figure 7:
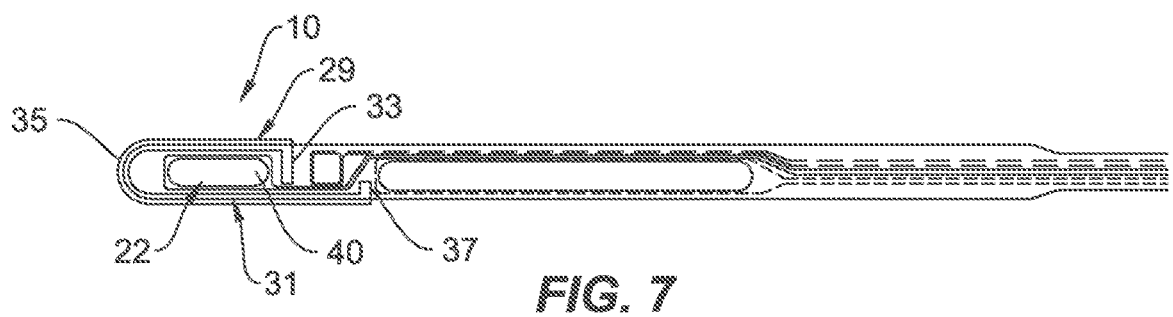
FIG. 7 is a mask plan view of one GOx sensor having a glucose sensing encasement of FIGS. 1-6.

FIG. 7 is a mask plan view of one glucose oxidase enzyme layer GOx sensor having a glucose sensing encasement 10 shown in simplified form in FIGS. 1-6. More particularly, glucose sensing encasement 10 is illustrated as a mask layup having a sensor 22 provided on an electrically conductive trace including a glucose oxidase enzyme sensing element, or electrode 40. Sensing element 40 is substantially encompassed by a circuitous and contiguous array of interlocking segment pairs including linear elongate interlocking segment pairs 29 and 31, semi-circular interlocking segment pair 35 extending between pairs 29 and 31, and a pair of transverse partial bulkhead interlocking segment pairs 33 and 37. Bulkhead segment pairs 33 and 37 provide just enough clearance for conductive traces on sensor 22 to communicate from sensor 40 with a power supply and data gathering computer having processing circuitry and memory (not shown).

Figure 8:
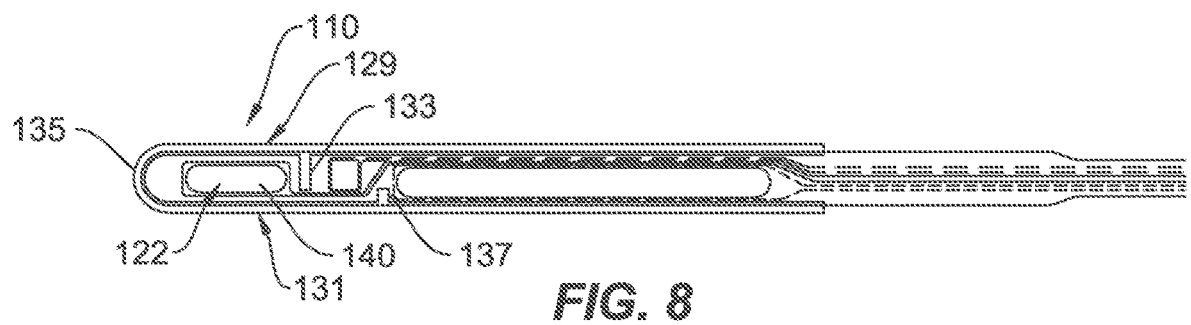
FIG. 8 is an optional glucose sensing encasement over that shown in FIG. 7.

FIG. 8 is an optional glucose sensing encasement 110 over that shown in FIG. 7. More particularly, encasement 110 includes linear elongate interlocking segment pairs 129 and 131 each contiguous at one end with a u-shaped interlocking segment pair 135 and a pair of partial bulkhead interlocking segment pairs 133 and 137 substantially encircling sensing element 140 of sensor 122 while providing a path for conductive traces to exit the substantially encircled region of sensing element 140.

Figure 9:
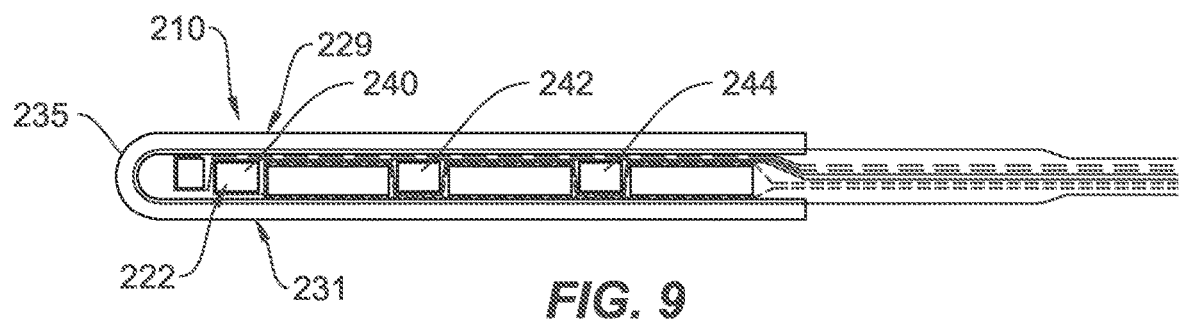
FIG. 9 is yet another optional glucose sensing encasement over that shown in FIGS. 7 and 8.

FIG. 9 is yet another optional glucose sensing encasement 210 over that shown in FIGS. 7 and 8. More particularly, encasement 210 includes linear elongate interlocking segment pairs 229 and 231 each contiguous at one end with a u-shaped interlocking segment pair 235 substantially encircling, or proximately interlocking the top and bottom membranes adjacent the individual sensing elements 240, 242, and 244 of sensor 222 while providing a path for conductive traces to exit the substantially encircled region of sensing element 240 by exiting the open end of a long u-shaped interlocking pair of elongate u-shaped elements.

Figure 10:
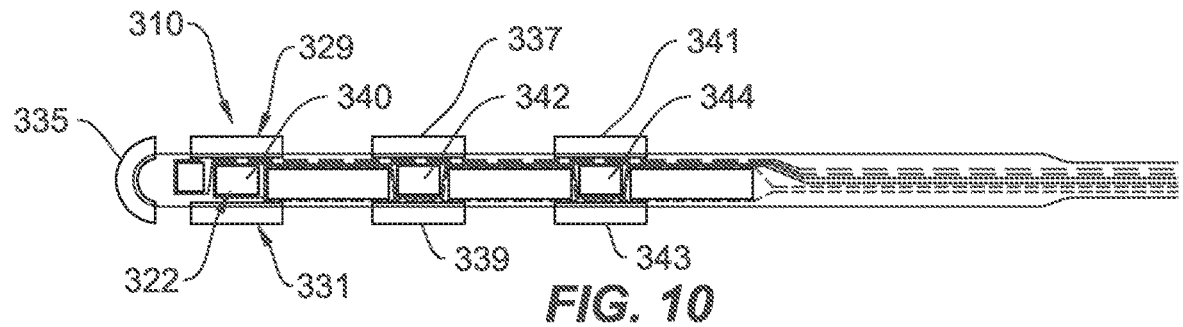
FIG. 10 is even another optional glucose sensing encasement over that shown in FIGS. 7-9 showing a discrete spaced-apart array of interlocking segments forming a zipper proximate each sensing electrode.

FIG. 10 is even another optional glucose sensing encasement 310 over that shown in FIGS. 7-9 and including interlocking segment pairs 329, 331, 335, 337, 339, 341, and 343 forming a staggered pair of adjacent interlocking segment pairs of lateral sides of each sensing element 340, 342, and 344 of sensor 322 to provide a zipper-like interlocking array of segment pairs proximate each sensing electrode. More particularly, interlocking segment pairs are provided along each sensor electrode.

Figure 11:
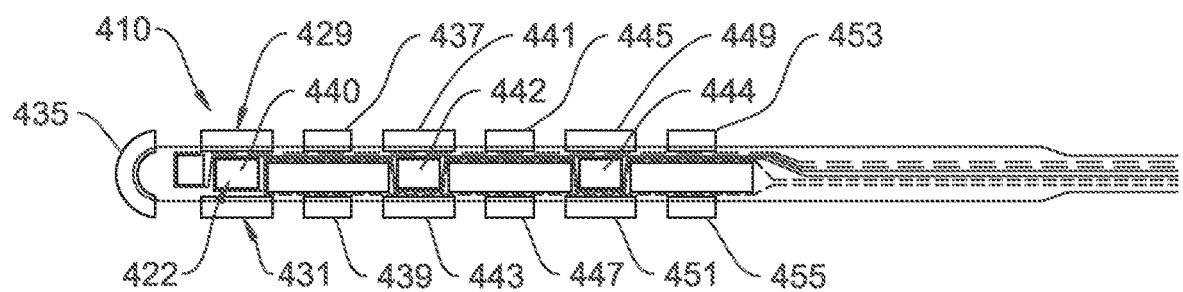
FIG. 11 is yet even another optional glucose sensing encasement over that shown in FIGS. 7-10 showing a discrete spaced-apart array of interlocking segments forming a zipper proximate each sensing electrode.

FIG. 11 is yet even another optional glucose sensing encasement 410 over that shown in FIGS. 7-10 and including interlocking segment pairs 429, 431, 435, 437, 439, 441, 443, 445, 447, 449, 451, and 453, 455 forming a staggered pair of adjacent interlocking segment pairs of lateral sides of each sensing element 440, 442, and 444 of sensor 422 to provide a zipper-like interlocking array of segment pairs proximate each sensing electrode.

Segment pairs 437, 439, 445, 447, and 453, 455 of FIG. 11 are spaced adjacent, but offset from sensor elements 440, 442 and 442, 444 showing a discrete spaced-apart array of interlocking segments forming a zipper that further edge supports the top and bottom membranes covering the sensing electrode 440, 442, and 444. More particularly, interlocking segment pairs are provided along each sensor electrode, and further interlocking segment pairs are provided between adjacent electrodes in order to lock the top and bottom membranes, or layers together and prevent peeling of top layer 14 from bottom layer 12 (see FIG. 1) that would otherwise negatively influence side diffusion of glucose as used in-vivo.

The terms "a", "an", and "the" as used in the claims herein are used in conformance with long-standing claim drafting practice and not in a limiting way. Unless specifically set forth herein, the terms "a", "an", and "the" are not limited to one of such elements, but instead mean "at least one".

While the subject matter of this application was motivated in addressing a glucose biosensor encasement, it is in no way so limited. The disclosure is only limited by the accompanying claims as literally worded, without interpretative or other limiting reference to the specification, and in accordance with the doctrine of equivalents. Other aspects and implementations of other biosensor encasements are contemplated.

In compliance with the statute, the various embodiments have been described in language more or less specific as to structural and methodical features. It is to be understood, however, that the various embodiments are not limited to the specific features shown and described, since the means herein disclosed comprise disclosures of putting the various embodiments into effect. The various embodiments are, therefore, claimed in any of its forms or modifications within the proper scope of the appended claims appropriately interpreted in accordance with the doctrine of equivalents.

What is claimed is:

1. A glucose biosensor encasement, comprising:
 a first flexible membrane having a first interlocking elongate segment;
 a second flexible membrane having a second interlocking elongate segment and the first and second interlocking elongate segments cooperate to form an elongate undercut mechanical interlock along a peripheral edge between the first flexible membrane and the second flexible membrane with the first interlocking elongate segment and cooperate to provide a cavity between the first membrane and the second membrane configured to receive a glucose sensor and provide resistance to edge peeling about a periphery of the cavity to realize a desired sensitivity for the glucose sensor; and
 at least one of the first membrane and the second membrane comprising a semi-permeable portion comprising a diffusion layer configured to regulate diffusion characteristics of glucose through the membrane to realize a sensitivity for a sensor in the cavity; wherein:
 the first interlocking segment comprises an elongate ridge and the second interlocking segment comprises a channel having an ensmalled distal width and an enlarged proximal width complementary to the elongate ridge and interlocking in assembly.

2. The encasement of claim 1, wherein the first interlocking segment is part of the first membrane and the second interlocking segment is part of the second membrane and the first interlocking segment and the second interlocking segment form a dovetail joint between the first membrane and the second membrane.

3. The encasement of claim 1, wherein the first interlocking segment and the second interlocking segment form a u-shaped interlocking seam between the first membrane and the second membrane extending about an outer periphery of the cavity.

4. The encasement of claim 1, wherein a plurality of discrete first interlocking segments and a complementary plurality of discrete second interlocking segments are provided spaced apart about an outer periphery of the cavity between the first membrane and the second membrane.

5. The encasement of claim 1, wherein the first interlocking segment and the second interlocking segment are each provided respectively proximate an outer periphery of the first membrane and the second membrane.

6. The encasement of claim 1, wherein the first membrane and the second membrane cooperate to provide a plurality of spaced-apart sensor cavities, at least one pair of first interlocking segment and second interlocking segment provided proximate each sensor cavity.

7. The encasement of claim 1, wherein the first interlocking segment and the second interlocking segment substantially encompass the sensor cavity.

8. The encasement of claim 1, wherein the first interlocking segment comprises an elongate trench having an ensmalled cross-sectional portion distal of the first membrane and the second interlocking segment comprises an elongate rib having an enlarged cross-sectional portion proximal of the first membrane.

9. The encasement of claim 8, wherein the second interlocking segment is a mask layer deposited at least in part within the trench.

10. A glucose biosensor package, comprising:
   a first flexible membrane having a first interlocking elongate portion;
   a second flexible membrane having a second interlocking elongate portion having an elongate undercut mechanical interlock along a peripheral edge of the first flexible membrane and the second flexible membrane that cooperates with the first interlocking elongate portion of the first membrane to physically lock together the first membrane and the second membrane and provide a cavity between the first membrane and the second membrane configured to receive a biosensor resistant to edge peeling;
   a biosensor having at least one sensing element contained in the cavity; and
   at least one of the first membrane and the second membrane comprising a semi-permeable portion comprising a diffusion layer configured to regulate diffusion characteristics of glucose through the membrane to realize a sensitivity for the biosensor in the cavity; wherein:
   the first interlocking portion comprises an elongate ridge and the second interlocking portion comprises an elongate channel having an ensmalled distal width and an enlarged proximal width complementary to the elongate ridge and interlocking in assembly.

11. The glucose biosensor package of claim 10, wherein the first interlocking portion of the first membrane comprises at least one elongate interlocking segment and the second interlocking portion of the second layer comprises a second complementary at least one elongate interlocking segment of the second membrane.

12. The glucose biosensor package of claim 11, wherein the second membrane comprises a semi-permeable portion proximate a sensing element of the biosensor.

13. The glucose biosensor package of claim 10, wherein the first membrane comprises an insulating base layer and a pair of deposited interlocking rail segments each affixed in aligned interlocking relation with the base layer with in respective recess slots.

14. The glucose biosensor package of claim 10, wherein the elongate ridge and the elongate channel form an elongate dovetail joint.

* * * * *